United States Patent [19]
Greeb

[11] Patent Number: 4,772,424
[45] Date of Patent: Sep. 20, 1988

[54] SHAMPOO CONTAINING MIXTURES OF SULFATE AND/OR SULFONATE, SARCOSINATE AND BETAINE SURFACTANTS

[75] Inventor: Henry R. Greeb, Cincinnati, Ohio

[73] Assignee: The Proctor & Gamble Company, Cincinnati, Ohio

[21] Appl. No.: 926,486

[22] Filed: Nov. 3, 1986

Related U.S. Application Data

[63] Continuation-in-part of Ser. No. 816,917, Jan. 8, 1986, abandoned.

[51] Int. Cl.$^4$ .......... C11D 1/10; C11D 1/29; C11D 1/90

[52] U.S. Cl. .......... 252/546; 252/544; 252/550; 252/551; 252/554; 252/DIG. 13; 252/DIG. 14

[58] Field of Search .......... 252/546, 544, 550, 551, 252/554, DIG. 5, DIG. 13, DIG. 14; 424/70

[56] References Cited

U.S. PATENT DOCUMENTS

| | | | |
|---|---|---|---|
| 3,085,067 | 4/1963 | Anderson | 252/153 |
| 3,980,769 | 9/1976 | Ghilardi et al. | 424/70 |
| 4,110,263 | 8/1978 | Lindermann et al. | 252/545 |
| 4,246,131 | 1/1981 | Lohr | 252/153 |
| 4,379,753 | 4/1983 | Bolich | 252/106 |
| 4,554,098 | 11/1985 | Klisch et al. | 252/547 |
| 4,578,216 | 3/1986 | Fugii et al. | 252/542 |
| 4,595,526 | 8/1986 | Lai | 252/545 |
| 4,617,148 | 10/1986 | Shields | 252/547 |

FOREIGN PATENT DOCUMENTS

| | | |
|---|---|---|
| 141797 | 7/1985 | Japan . |
| 611972 | 1/1961 | Canada . |

OTHER PUBLICATIONS

Japanese Published Application J5 6163-198 to Lion Corp. (abstract only).
Japanese Published Application 60-141797 to Shiseido (abstract plus Japanese language copy).

*Primary Examiner*—Prince E. Willis
*Attorney, Agent, or Firm*—Richard C. Witte; Jack D. Schaeffer; Douglas C. Mohl

[57] ABSTRACT

Cleaning compositions are disclosed which comprise a mixture of betaine, sarcosinate and alkyl sulfate or sulfonate surfactants.

12 Claims, No Drawings

SHAMPOO CONTAINING MIXTURES OF SULFATE AND/OR SULFONATE, SARCOSINATE AND BETAINE SURFACTANTS

CROSS REFERENCE TO RELATED APPLICATION

This is a continuation-in-part of my copending application Ser. No. 816,917, filed Jan. 8, 1986, now abandoned.

TECHNICAL FIELD

The present invention concerns cleaning compositions which are isotropic and which utilize a particular mixture of surfactants.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of hair necessitates it being shampooed with frequent regularity.

Frequent shampooing causes users to want shampoo forms which are convenient to use and have pleasing aesthetics. A convenient product form for use in the shampooing process and one widely used is a "concentrate" or gel type form. These forms generally have a directionally higher surfactant level than their liquid and lotion counterparts (e.g., 21–22% vis-a-vis 15–18%). However, their gel type structure is achieved primarily through the use of a gelling or thickening polymeric material and not high surfactant levels. The use of surfactant levels greater than the 21–22% level is desirable to achieve greater cleaning power.

A pleasing aesthetic attribute desired by many users in their shampoo is for it to be clear (i.e., isotropic). Achieving an isotropic composition with a surfactant concentration in the 24–40% range and higher is something that is desirable for the reasons given above but not easily achieved.

Many references disclose compositions which contain high levels of surfactant but not all claim to be isotropic and many probably do not represent compositions which had actually been prepared. Among such references is Japanese Published Application J No. 60141797, July 26, 1985 disclosing a gel composition comprising an ethoxylated alkyl sulfate and a betaine. Other references have similar disclosures. Japanese Published Application J No. 6163-198, December 15, 1981 discloses mixtures of anionic sulfate surfactants and betaine surfactants. U.S. Pat. No. 3,980,769, Sept. 14, 1976 to Ghilardi et al. discloses detergent composition containing a mixture of anionic and amphoteric surfactants. U.S. Pat. No. 4,110,263, Aug. 29, 1978 to Lindemann et al. discloses cleaning compositions containing anionic and amphoteric surfactants. U.S. Pat. No. 4,246,131, Jan. 20, 1981 to Lohr discloses water free surfactant compositions comprising a mixture of betaine and alkyl sulfate surfactants wherein the surfactants comprise at least 40% of the compositions. U.S. Pat. No. 4,329,334, May 11, 1982 to Su et al. discloses shampoo compositions which contain a mixture of anionic and amphoteric surfactants.

While the prior art, such as that discussed above, discloses compositions containing high surfactant levels, there still is the need for compositions containing not only high surfactant levels but which also are isotropic.

The present inventor has surprisingly found that such compositions can be prepared by combining alkyl sulfate or sulfonate surfactants with betaine and sarcosinate surfactants.

It is an object, therefore, of the present invention to provide compositions which contain high levels of surfactant.

It is a further object of the present invention to provide such compositions which are isotropic.

It is a further object of the present invention to provide such compositions which have sufficient viscosity to be a gel or concentrate.

It is still a further object of the present invention to provide such compositions which lather well and clean well.

These and other objectives will become readily apparent from the detailed description which follows.

All percentages and ratios herein are by weight unless otherwise specified.

SUMMARY OF THE INVENTION

The present invention relates to cleaning compositions comprising from about 15% to about 30% of an alkyl sulfate or alkyl sulfonate surfactant, from about 0.8% to about 15% of a betaine surfactant, from about 0.5% to about 15% of a sarcosinate surfactant and the remainder water, wherein the total surfactant level is in the range of about 24% to about 40% and if an alkoxide linkage is present in the alkyl group of the sulfate or sulfonate surfactant it is less than 3 alkoxide units in length. These as well as optional components are described in detail below. The compositions have a viscosity of from about 5,000 to about 40,000 centipoise.

DETAILED DESCRIPTION OF THE INVENTION

The essential components of the present invention are: Alkyl Sulfate or Alkyl Sulfonate Surfactant Synthetic alkyl sulfate or sulfonate surfactants can be exemplified by the alkali metal salts of organic sulfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; ammonium, sodium, potassium or triethanol amine salts of sulfuric acid esters of the reaction product of 1 mole of a higher fatty alcohol (e.g., tallow or coconut oil alcohols) and 1 to 3 moles of ethylene oxide; sodium or potassium salts of alkyl phenol ethylene oxide ether sulfate with 1 to 3 units of ethylene oxide per molecular and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; and others known in the art. As used hereinafter the term "alkyl" includes alkyls which have an acyl group attached and/or those which have alkoxide groups combined with the alkyl moiety. Specific preferred surfactants for use herein include ammonium lauryl sulfate, ammonium laureth(2) sulfate and mixtures thereof.

The alkyl sulfate or sulfonate surfactant or mixtures thereof is used in the compositions of the present invention at a level of from about 15% to about 30%, preferably from about 18% to about 25%.

Betain Surfactant

Examples of betaines useful herein include the high alkyl betaines such as coco dimethyl carboxymethyl betaine ("cocobetaine"), lauryl dimethyl carboxymethyl betaine, lauryl dimethyl alpha-carboxy-ethyl betaine, cetyl dimethyl carboxymethyl betain, lauryl bis-(2-hydroxy-ethyl) carboxy methyl betaine, stearyl bis-(2-hydroxy-propyl) carboxymethyl betaine, oleyl dimethyl gamma-carboxypropyl betaine, lauryl bis-(2-hydroxypropyl) alpha-carboxyethyl betaine, etc. Other betaines are the sulfobetaines which may be represented by coco dimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfobetaines, wherein an $RCONH(CH_2)_x$ radical is attached to the nitrogen atoms of the betaine are also useful in this invention. The carboxy betaines and the amido betaines are preferred for use in the compositions of this invention. Specific preferred betaines include cocamidopropyl betaine, cocobetaine, myristyl amidopropyl betaine and mixtures thereof.

The betaines are present in the compositions of the present invention at a level of from about 0.8% to about 15%, preferably from about 0.9% to about 8%.

Sarcosinate Surfactant

N-acyl sarcosinates are used in the present invention and are the salts of condensation products of fatty acids with sarcosine. They can be represented

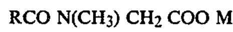

$RCO\ N(CH_3)\ CH_2\ COO\ M$ wherein M may be sodium, potassium, ammonium or triethanolamine. Specific preferred sarcosinates include sodium oleoyl sarcosinate, sodium cocoyl sarcosinate, sodium lauroyl sarcosinate and mixtures thereof.

The acyl sarcosinates useful herein are described in U.S. Pat. No. 3,085,067, April 9, 1963 to Anderson (incorporated herein by reference). Anderson indicates that in addition to providing cleaning and latering benefits, the surfactant can also provide conditioning.

The sarcosinate surfactant is present in the composition of this invention at a level of from about 0.5% to about 15%, preferably from about 0.5% to about 8%.

Other examples of the alkyl sulfate or alkyl sulfonate, betaine and sarcosinate surfactants can be found in McCutcheon's Emulsifiers & Detergents North American Edition, 1983, published by Allured Publishing Corporation, incorporated herein by reference.

Water

Water is the last essential component of the present invention and forms the remainder of the compositions. The water is preferably deionized and is preferably used at levels of from about 45% to about 76%.

Optional Components

The compositions herein can contain a variety of non-essential optional components suitable for rendering such compositions more acceptable. Such conventional optional ingredients are well known to those skilled in the art, e.g., preservatives such as benzyl alcohol, methyl paraben, propyl paraben and imidazolidinyl urea; cationic surfactants such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; styling polymers such as polyvinyl pyrrolidone (PVP) or a copolymer of PVP and vinyl acetate; thickeners and viscosity modifier such as a diethanolamide of a long chain fatty acid (e.g., PEG 3 lauramide), block polymers of ethylene oxide and propylene oxide such as Pluronic F88 offered by BASF Wyandotte, sodium chloride, sodium sulfate, polyvinyl alcohol, and ethyl alcohol; pH adjusting agents such as citric acid, succinic acid, phosphoric acid, sodium hydroxide, sodium carbonate, etc.; silicone fluids; perfumes; dyes; hydrotropes such as ammonium xylene sulfonate or potassium toluene sulfonate; and, sequestering agents such as disodium ethylenediamine tetraacetate. Such agents generally are used individually at a level of from about 0.01% to about 10%, preferably from about 0.1% to about 5.0% by weight of the composition.

The pH of the present composition is not critical but generally is in the range of from 4 to about 8.

The viscosity of the present compositions is preferably sufficiently high to give the compositions a gel type consistency. When a gel, the viscosity of the composition is generally from about 5,000 centipoise to about 40,000 centipoise, preferably from about 10,000 centipoise to about 40,000 centipoise. The compositions of the present invention are non-newtonian solutions which exhibit varying viscosities when sheared. The visocity indicated is the viscosity obtained at a shear rate of $10^{-1}$ seconds with the temperature being controlled at 80° F.

METHOD OF MANUFACTURE

A method for making the present compositions is described below in the Examples.

INDUSTRIAL APPLICABILITY

The present compositions are used in a conventional manner for cleaning human hair. From about 0.1 g to about 15 g of a composition is applied to hair that has been wetted, generally with water, worked through the hair and then rinsed out.

Although the present compositions are ideally suited for cleaning human hair, they may also be used for overall body cleaning and the cleaning of hard surfaces of domestic animals among many other things.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLE I

The following is a composition representative of the present invention.

| Component | Wt. % |
|---|---|
| Ammonium Laureth (2) Sulfate | 20.490% |
| Cocamidopropylbetaine | 5.000 |
| Sodium Lauroyl Sarcosinate | 3.000 |

-continued

| Component | Wt. % |
|---|---|
| Cocamide DEA | 2.300 |
| Ethanol | 0.540 |
| Fragrance | 0.500 |
| Sodium Phosphate | 0.500 |
| Di Sodium Phosphate | 0.380 |
| Dye Solution (1% aqueous solution) | 0.250 |
| EDTA | 0.100 |
| Preservative (1.5% aqueous solution) | 0.093 |
| Water | 66.847 |
| | 100.000% |

EXAMPLE II

The following is another composition representative of the present invention.

| Component | Wt. % |
|---|---|
| Ammonium Laureth (2) Sulfate | 20.490% |
| Cocamidopropylbetaine | 4.000 |
| Cocamide DEA | 2.300 |
| Sodium Lauroyl Sarcosinate | 2.000 |
| Ethanol | 0.540 |
| Fragrance | 0.500 |
| Sodium Phosphate | 0.500 |
| Di Sodium Phosphate | 0.380 |
| Dye Solution (1% aqueous solution) | 0.250 |
| EDTA | 0.100 |
| Benzophenone-2 | 0.060 |
| Preservative (1.5% aqueous solution) | 0.033 |
| Water | 68.847 |
| | 100.000% |

The above composition can be made by making a premix of the ethanol and the benzophenone. While this mixture is mixing, water is added to a mix tank of suitable size with 30% aqueous solutions of the sarcosinate and the betaine being then added and this surfactant mixture is heated to 160° F. The phosphates and EDTA are then added to the surfactant mixture followed by the sulfate surfactant as a 71% solution, the ethanol/-benzophenone premix and the amide. This mixture is cooled to below 120° F. with the fragrance and the preservative then added. The mixture is finally cooled to room temperature.

EXAMPLE III

Given below is another composition representative of the present invention.

| Component | Wt. % |
|---|---|
| Ammonium Laureth (2) Sulfate | 20.490% |
| Myristylamidopropylbetaine | 4.000 |
| Cocamide DEA | 2.300 |
| Sodium Lauroyl Sarcosinate | 2.000 |
| Ethanol | 0.540 |
| Fragrance | 0.500 |
| Sodium Phosphate | 0.500 |
| Di Sodium Phosphate | 0.380 |
| Dye Solution (1% aqueous solution) | 0.250 |
| EDTA | 0.100 |
| Benzophenone-2 | 0.060 |
| Preservative (1.5% aqueous solution) | 0.033 |
| Water | 68.847 |
| | 100.000 |

EXAMPLE IV

This is another composition representative of the present invention.

| Component | Wt. % |
|---|---|
| Ammonium Laureth (2) Sulfate | 20.490% |
| Laurylmyristylamidopropylbetaine | 5.000 |
| Sodium Lauroyl Sarcosinate | 4.000 |
| Cocamide DEA | 2.300 |
| Ethanol | 0.540 |
| Fragrance | 0.500 |
| Sodium Phosphate | 0.500 |
| Di Sodium Phosphate | 0.380 |
| Dye Solution (1% aqueous solution) | 0.250 |
| EDTA | 0.100 |
| Benzophenone-2 | 0.060 |
| Preservative (1.5% aqueous solution) | 0.033 |
| Water | 68.847 |
| | 100.000% |

EXAMPLE V

The composition given below is another representation of the present invention.

| Component | Wt. % |
|---|---|
| Ammonium Laureth (2) Sulfate | 20.490% |
| Sodium Oleoyl Sarcosinate | 8.000 |
| Cocamide DEA | 2.300 |
| Laurylmyristylamidopropylbetaine | 2.000 |
| Ethanol | 0.540 |
| Fragrance | 0.500 |
| Sodium Phosphate | 0.500 |
| Di Sodium Phosphate | 0.380 |
| Dye Solution (1% aqueous solution) | 0.250 |
| EDTA | 0.100 |
| Benzophenone-2 | 0.060 |
| Preservative (1.5% aqueous solution) | 0.033 |
| Water | 68.847 |
| | 100.000% |

EXAMPLE VI

The following is another composition representative of the present invention.

| Component | Wt. % |
|---|---|
| Ammonium Laureth (2) Sulfate | 20.490% |
| Cocobetaine | 4.000 |
| Cocamide DEA | 2.300 |
| Sodium Cocoyl Sarcosinate | 2.000 |
| Ethanol | 0.540 |
| Fragrance | 0.500 |
| Sodium Phosphate | 0.500 |
| Di Sodium Phosphate | 0.380 |
| Dye Solution (1% aqueous solution) | 0.250 |
| EDTA | 0.100 |
| Benzophenone-2 | 0.060 |
| Preservative (1.5% aqueous solution) | 0.033 |
| Water | 68.847 |
| | 100.000% |

The foregoing compositions are all isotropic and have viscosities in the range of 5,000 to about 40,000 centipoise.

What is claimed is:

1. An isotropic cleaning composition comprising:

(a) from about 15% to about 30% of a surfactant selected from the group consisting of alkyl or ethoxylated alkyl sulfates, alkyl or ethoxylated alkyl sulfonates and mixtures thereof;

(b) from bout 0.8% to about 15% of a betaine surfactant or mixtures thereof;

(c) from about 0.5% to about 15% of a sarcosinate surfactant or mixtures thereof; and (d) water wherein the total surfactant level is in the range of from about 24% to about 40%, if an alkoxide linkage is present in the alkyl group of the sulfate or sulfonate surfactant it is less than 3 alkoxide units in length and the viscosity of said composition is from about 5,000 to about 40,000 centipoise.

2. A composition according to claim 1 wherein (a) is an alkyl sulfate.

3. A composition according to claim 2 wherein the betaine is selected from the group consisting of coco betaine, lauryl/myristyl amido propyl betaine, and cocamidopropyl betaine, myristyl propyl betaine and mixtures thereof.

4. A composition according to claim 3 wherein the sarcosinate surfactant is selected from the group consisting of sodium lauroyl sarcosinate, sodium oleyl sarcosinate, sodium cocoyl sarcosinate and mixtures thereof.

5. A composition according to claim 4 wherein the amount of the alkyl sulfate surfactant is from 18% to about 25%.

6. A composition according to claim 5 wherein the amount of the betaine surfactant is from about 0.8% to about 8%.

7. A composition according to claim 6 wherein the amount of the sarcosinate surfactant is from about 0.5% to about 8%.

8. A composition according to claim 7 wherein the alkyl sulfate surfactant is selected from the group consisitng of ammonium lauryl sulfate, ammonium laureth (2) sulfate and mixtures thereof.

9. A method of shampooing human hair comprising:

(a) applying from about 0.1 g to about 15 g of a composition according to claim 1 to hair that has been wetted;

(b) working said composition through said hair; and (c) rinsing said composition from said hair.

10. A method according to claim 9 wherein the composition is according to claim 2.

11. A method according to claim 10 wherein the composition is according to claim 7.

12. A method according to claim 10 wherein the composition is according to claim 8.

* * * * *